(12) United States Patent
Plos et al.

(10) Patent No.: US 7,651,535 B2
(45) Date of Patent: Jan. 26, 2010

(54) DYEING OF IN PARTICULAR HUMAN KERATIN MATERIALS BY DRY THERMAL TRANSFER OF A DIRECT ANTHRAQUINONE DYE, COMPOSITION COMPRISING THE SAID DYE AND ITS METHOD OF PREPARATION

(75) Inventors: Grégory Plos, Tokyo (JP); Luc Gourlaouen, Asnières (FR); Jean-Dominique Bazin De Bezons, Montrouge (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 11/795,226

(22) PCT Filed: Feb. 28, 2006

(86) PCT No.: PCT/EP2006/003296

§ 371 (c)(1),
(2), (4) Date: Feb. 5, 2008

(87) PCT Pub. No.: WO2006/089809

PCT Pub. Date: Aug. 31, 2006

(65) Prior Publication Data

US 2008/0168608 A1 Jul. 17, 2008

Related U.S. Application Data

(60) Provisional application No. 60/681,456, filed on May 17, 2005.

(30) Foreign Application Priority Data

Feb. 28, 2005 (FR) .................................. 05 02030

(51) Int. Cl.
*A61Q 5/10* (2006.01)
(52) U.S. Cl. ....................... 8/405; 8/406; 8/408; 8/552; 8/643
(58) Field of Classification Search ...................... 8/405, 8/406, 408, 552, 643
See application file for complete search history.

(56) References Cited

U.S. PATENT DOCUMENTS

| | | | |
|---|---|---|---|
| 2,047,398 A | 7/1936 | Voss et al. |
| 2,723,248 A | 11/1955 | Wright |
| 3,579,629 A | 5/1971 | Pasero et al. |
| 3,597,468 A | 8/1971 | Kalopssis et al. |
| 3,617,165 A | 11/1971 | Kalopissis |
| 3,716,633 A | 2/1973 | Viout et al. |
| 3,770,683 A | 11/1973 | Barabas et al. |
| 3,810,977 A | 5/1974 | Levine et al. |
| 3,836,537 A | 9/1974 | Boerwinkle et al. |
| 3,867,094 A | 2/1975 | Kalopissis et al. |
| 3,910,862 A | 10/1975 | Barabas et al. |
| 3,925,542 A | 12/1975 | Viout et al. |
| 3,929,735 A | 12/1975 | Barabas |
| 3,946,749 A | 3/1976 | Papantoniou |
| 3,960,476 A | 6/1976 | Ghilardi et al. |
| 3,963,764 A | 6/1976 | Kalopissis et al. |
| 3,966,403 A | 6/1976 | Papantoniou et al. |
| 3,966,404 A | 6/1976 | Papantoniou et al. |
| 3,981,676 A | 9/1976 | Ghilardi et al. |
| 3,981,678 A | 9/1976 | Ghilardi et al. |
| 3,984,402 A | 10/1976 | Kalopissis et al. |
| 3,990,459 A | 11/1976 | Papantoniou |
| 4,003,699 A | 1/1977 | Rose et al. |
| 4,007,747 A | 2/1977 | Kalopissis et al. |
| 4,045,170 A | 8/1977 | Kalopissis et al. |
| 4,046,786 A | 9/1977 | Kalopissis et al. |
| 4,070,533 A | 1/1978 | Papantoniou et al. |
| 4,076,912 A | 2/1978 | Papantoniou et al. |
| 4,128,631 A | 12/1978 | Lundmark et al. |
| 4,129,711 A | 12/1978 | Viout et al. |
| 4,137,208 A | 1/1979 | Elliott |
| 4,165,367 A | 8/1979 | Chakrabarti |
| RE30,199 E | 1/1980 | Rose et al. |
| 4,223,009 A | 9/1980 | Chakrabarti |
| 4,282,203 A | 8/1981 | Jacquet et al. |
| 4,289,752 A | 9/1981 | Mahieu et al. |
| 4,521,504 A | 6/1985 | Sakuma et al. |
| 4,608,392 A | 8/1986 | Jacquet et al. |
| 4,693,935 A | 9/1987 | Mazurek |
| 4,728,571 A | 3/1988 | Clemens et al. |
| 4,925,667 A | 5/1990 | Fellows et al. |
| 4,972,037 A | 11/1990 | Garbe et al. |
| 5,000,948 A | 3/1991 | Nandagiri et al. |
| 5,061,289 A | 10/1991 | Clausen et al. |
| 5,158,762 A | 10/1992 | Pierce |
| 5,380,340 A | 1/1995 | Neunhoeffer et al. |

(Continued)

FOREIGN PATENT DOCUMENTS

DE 2 330 956 1/1974

(Continued)

OTHER PUBLICATIONS

STIC Search Report dated Aug. 22, 2008.*

(Continued)

*Primary Examiner*—Eisa B Elhilo
(74) *Attorney, Agent, or Firm*—Finnegan, Henderson, Farabow, Garrett & Dunner, L.L.P.

(57) ABSTRACT

The subject of the present invention is the use, for dyeing in particular human keratin materials, of a specific direct anthraquinone dye by dry thermal transfer.

Its subject is furthermore a method for dyeing keratin materials, in which at least one direct anthraquinone dye contained in a dry composition is applied to or close to the keratin materials, and a source of heat is applied, causing the thermal transfer of the direct dye(s) at the surface and/or inside the keratin materials.

It relates furthermore to the dry composition and a method for preparing it.

28 Claims, No Drawings

U.S. PATENT DOCUMENTS

| | | |
|---|---|---|
| 5,506,315 A | 4/1996 | Meyer et al. |
| 5,534,267 A | 7/1996 | Neunhoeffer et al. |
| 5,538,717 A | 7/1996 | La Poterie |
| RE35,550 E | 7/1997 | Jongewaard et al. |
| 5,663,366 A | 9/1997 | Neunhoeffer et al. |
| 5,690,921 A | 11/1997 | Lang et al. |
| 5,708,151 A | 1/1998 | Mockli |
| 5,739,195 A | 4/1998 | Kroker et al. |
| 5,766,576 A | 6/1998 | Lowe et al. |
| 5,792,221 A | 8/1998 | Lagrange et al. |
| 5,931,168 A | 8/1999 | Abercrombie et al. |
| 5,961,664 A * | 10/1999 | Anderson ................ 8/405 |
| 6,099,592 A | 8/2000 | Vidal et al. |
| 6,106,813 A | 8/2000 | Mondet et al. |
| 6,166,093 A | 12/2000 | Mougin et al. |
| 6,211,400 B1 | 4/2001 | Berghofer et al. |
| 6,284,003 B1 | 9/2001 | Rose et al. |
| 6,319,959 B1 | 11/2001 | Mougin et al. |
| 6,338,741 B1 | 1/2002 | Vidal et al. |
| 6,372,876 B1 | 4/2002 | Kim et al. |
| 6,395,265 B1 | 5/2002 | Mougin et al. |
| 6,586,622 B2 | 7/2003 | Berghofer et al. |
| 6,645,258 B2 | 11/2003 | Vidal et al. |
| 6,770,271 B2 | 8/2004 | Mondet et al. |
| 6,824,570 B2 | 11/2004 | Vidal et al. |
| 6,835,211 B1 | 12/2004 | Rose et al. |
| 6,881,230 B2 | 4/2005 | Vidal |
| 6,884,265 B2 | 4/2005 | Vidal et al. |
| 6,884,267 B2 | 4/2005 | Vidal et al. |
| 6,893,471 B2 | 5/2005 | Vidal |
| 7,001,436 B2 | 2/2006 | Vidal et al. |
| 7,022,143 B2 | 4/2006 | Vidal et al. |
| 7,060,110 B2 | 6/2006 | Vidal et al. |
| 7,063,834 B2 | 6/2006 | Mougin et al. |
| 7,077,873 B2 | 7/2006 | David et al. |
| 7,179,300 B2 | 2/2007 | Legrand et al. |
| 7,261,743 B2 | 8/2007 | Plos et al. |
| 2002/0095732 A1 | 7/2002 | Kravtchenko et al. |
| 2002/0150546 A1 | 10/2002 | Mougin et al. |
| 2002/0197224 A1 | 12/2002 | Slusarewicz |
| 2003/0024544 A1 | 2/2003 | Thiebaut |
| 2003/0084516 A9 | 5/2003 | Kravtchenko et al. |
| 2003/0087111 A1 | 5/2003 | Hubbell et al. |
| 2003/0099691 A1 | 5/2003 | Lydzinski et al. |
| 2003/0099692 A1 | 5/2003 | Lydzinski et al. |
| 2003/0135937 A1 | 7/2003 | Barrass et al. |
| 2003/0175226 A1 | 9/2003 | Patel et al. |
| 2004/0009211 A1 | 1/2004 | Roreger et al. |
| 2004/0016064 A1 | 1/2004 | Vena et al. |
| 2004/0093676 A1 | 5/2004 | Vidal et al. |
| 2004/0127692 A1 | 7/2004 | David et al. |
| 2004/0170590 A1 | 9/2004 | Fahnestock et al. |
| 2004/0200009 A1 | 10/2004 | Vidal |
| 2004/0253283 A1 | 12/2004 | Muller et al. |
| 2005/0008589 A1 | 1/2005 | Legrand et al. |
| 2005/0025736 A1 | 2/2005 | Jachowicz et al. |
| 2005/0039268 A1 | 2/2005 | Plos et al. |
| 2005/0050648 A1 | 3/2005 | Legrand et al. |
| 2005/0249763 A1 | 11/2005 | Legendre et al. |
| 2006/0000033 A1 | 1/2006 | Rollat-Corvol et al. |
| 2008/0247977 A1 | 10/2008 | Le Gendre et al. |
| 2008/0263786 A1 | 10/2008 | Schmenger et al. |

FOREIGN PATENT DOCUMENTS

| | | |
|---|---|---|
| DE | 23 59 399 | 6/1975 |
| DE | 38 43 892 | 6/1990 |
| DE | 41 33 957 | 4/1993 |
| DE | 42 34 743 | 4/1994 |
| DE | 195 43 988 | 5/1997 |
| DE | 196 13 941 | 10/1997 |
| DE | 10 2004 037 105 | 1/2005 |
| EP | 0 080 976 | 6/1983 |
| EP | 0 342 241 | 11/1989 |
| EP | 0 412 704 | 2/1991 |
| EP | 0 412 707 | 2/1991 |
| EP | 0 582 152 | 2/1994 |
| EP | 0 619 111 | 10/1994 |
| EP | 0 637 600 | 2/1995 |
| EP | 0 648 485 | 4/1995 |
| EP | 0 656 021 | 6/1995 |
| EP | 0 714 954 | 6/1996 |
| EP | 0 750 905 | 1/1997 |
| EP | 0 751 162 | 1/1997 |
| EP | 0 784 970 | 7/1997 |
| EP | 1 462 088 | 9/2004 |
| EP | 1 588 694 | 10/2005 |
| EP | 1 621 185 | 2/2006 |
| FR | 1 222 944 | 4/1959 |
| FR | 1 400 366 | 5/1963 |
| FR | 1 564 110 | 3/1968 |
| FR | 1 580 545 | 9/1969 |
| FR | 2 077 143 | 10/1971 |
| FR | 2 102 113 | 4/1972 |
| FR | 2 139 385 | 1/1973 |
| FR | 2 190 407 | 2/1974 |
| FR | 2 198 719 | 4/1974 |
| FR | 2 265 781 | 10/1975 |
| FR | 2 265 782 | 10/1975 |
| FR | 2 350 384 | 12/1977 |
| FR | 2 357 241 | 2/1978 |
| FR | 2 393 573 | 1/1979 |
| FR | 2 439 798 | 5/1980 |
| FR | 2 692 572 | 6/1992 |
| FR | 2 733 749 | 11/1996 |
| FR | 2 743 297 | 7/1997 |
| FR | 2 807 650 | 10/2001 |
| FR | 2 822 693 | 10/2002 |
| FR | 2 822 694 | 10/2002 |
| FR | 2 822 696 | 10/2002 |
| FR | 2 822 698 | 10/2002 |
| FR | 2 825 625 | 12/2002 |
| FR | 2 825 702 | 12/2002 |
| FR | 2 829 926 | 3/2003 |
| FR | 2 840 221 | 12/2003 |
| FR | 2 844 269 | 3/2004 |
| FR | 2 863 167 | 6/2005 |
| FR | 2 865 130 | 7/2005 |
| GB | 0 839 805 | 6/1960 |
| GB | 0 922 457 | 4/1963 |
| GB | 1 021 400 | 3/1966 |
| GB | 1 026 978 | 4/1966 |
| GB | 1 061 557 | 3/1967 |
| GB | 1 144 100 | 3/1969 |
| GB | 1 153 196 | 5/1969 |
| GB | 1 331 819 | 9/1973 |
| GB | 1 334 416 | 10/1973 |
| GB | 1 345 849 | 2/1974 |
| GB | 1. 402 051 | 8/1975 |
| GB | 1. 408 388 | 10/1975 |
| GB | 1. 572 555 | 7/1980 |
| GB | 1 572 626 | 7/1980 |
| JP | 60-030391 | 2/1985 |
| JP | 62-097886 A2 | 5/1987 |
| JP | 62-288656 A2 | 12/1987 |
| JP | 63-288787 A2 | 11/1988 |
| JP | 63-288788 A2 | 11/1988 |
| JP | 63-288789 A2 | 11/1988 |
| JP | 63-308072 | 12/1988 |
| JP | 01-178580 | 7/1989 |
| JP | 01-178581 | 7/1989 |
| JP | 2-019576 | 1/1990 |
| JP | 02-106394 | 4/1990 |
| JP | 03-007388 | 1/1991 |

| | | |
|---|---|---|
| JP | 03-007389 | 1/1991 |
| JP | 03-007390 | 1/1991 |
| JP | 03-007391 | 1/1991 |
| JP | 03-007392 | 1/1991 |
| JP | 04-275180 | 9/1992 |
| JP | 04-275181 | 9/1992 |
| JP | 04-275182 | 9/1992 |
| JP | 07-179070 A2 | 7/1995 |
| JP | 11-256062 A2 | 9/1999 |
| JP | 2002-47144 | 2/2002 |
| JP | 2003-137756 | 5/2003 |
| LU | 75370 | 2/1978 |
| LU | 75371 | 2/1978 |
| WO | WO 93/23009 | 11/1993 |
| WO | WO 93/23446 | 11/1993 |
| WO | WO 94/03510 | 2/1994 |
| WO | WO 94/08969 | 4/1994 |
| WO | WO 94/08970 | 4/1994 |
| WO | WO 94/12148 | 6/1994 |
| WO | WO 95/00578 | 1/1995 |
| WO | WO 95/01772 | 1/1995 |
| WO | WO 95/15144 | 6/1995 |
| WO | WO 96/06592 | 3/1996 |
| WO | WO 96/10593 | 4/1996 |
| WO | WO 96/15765 | 5/1996 |
| WO | WO 99/18067 | 4/1999 |
| WO | WO 01/28508 | 4/2001 |
| WO | WO 02/05789 | 1/2002 |
| WO | WO 02/30369 | 4/2002 |
| WO | WO 02/054997 | 7/2002 |
| WO | WO 02/078660 | 10/2002 |
| WO | WO 02/100369 | 12/2002 |
| WO | WO 02/100834 | 12/2002 |
| WO | WO 03/026597 | 4/2003 |
| WO | WO 03/041668 | 5/2003 |
| WO | WO 03/072075 | 9/2003 |
| WO | WO 03/075812 | 9/2003 |

OTHER PUBLICATIONS

Copending U.S. Appl. No. 11/795,640, filed Feb. 1, 2008.
Copending U.S. Appl. No. 11/765,641, filed Feb. 5, 2008.
English language Derwent Abstract of DE 10 2004 037105, dated Jan. 13, 2005.
English language Derwent Abstract of EP 0 080 976, Jun. 8, 1983.
English language Derwent Abstract of FR 2 357 241, Feb. 3, 1978.
English language Derwent Abstract of JP 01-178580, dated Jul. 14, 1989.
English language Derwent Abstract of JP 01-178581, dated Jul. 14, 1989.
English language Derwent Abstract of JP 02-106394, dated Apr. 18, 1990.
English language Derwent Abstract of JP 03-007388, dated Jan. 14, 1991.
English language Derwent Abstract of JP 03-007389, dated Jan. 14, 1991.
English language Derwent Abstract of JP 03-007390, dated Jan. 14, 1991.
English language Derwent Abstract of JP 03-007391, dated Jan. 14, 1991.
English language Derwent Abstract of JP 03-007392, dated Jan. 14, 1991.
English language Derwent Abstract of JP 04-275180, dated Sep. 30, 1992.
English language Derwent Abstract of JP 04-275181, dated Sep. 30, 1992.
English language Derwent Abstract of JP 04-275182, dated Sep. 30, 1992.
English language Derwent Abstract of JP 60-030391, dated Feb. 15, 1988.
English language Derwent Abstract of JP 63-308072, dated Dec. 15, 1988.
International Search report for PCT/EP2006/002586, dated Jun. 7, 2006, for corresponding U.S. Appl. No. 11/795,640.
International Search report for PCT/EP2006/002588, dated Jul. 4, 2006, for corresponding U.S. Appl. No. 11/795,641.
International Search report for PCT/EP2006/003296, dated Jul. 25, 2006, which corresponds to the present application.
Office Action mailed Oct. 23, 2008, in co-pending U.S. Appl. No. 11/795,640.
Office Action mailed Sep. 9, 2008, in co-pending U.S. Appl. No. 11/795,641.
STIC Search Report for U.S. Appl. No. 11/795,641, dated Aug. 27, 2008.
STIC Search Report for U.S. Appl. No. 11/795,640, dated Oct. 16, 2008.
Wenniger, J. et al., International Cosmetic Ingredient Dictionary and Handbook, 2000 ed., vol. 2, pp. 1744-1747.
Chemical Patent Abstracts Service, XP002351948, Accession No. 2003:371660 (May 15, 2003).
Clausen, et al., Hair Preparations, Wiley-Vch Verlag GmbH & Co., Weinheim, 2006, pp. 1-46.
Copending U.S. Appl. No. 11/362,787, filed Feb. 28, 2006.
Copending U.S. Appl. No. 11/362,790, filed Feb. 28, 2006.
Copending U.S. Appl. No. 11/362,791, filed Feb. 28, 2006.
English language Abstract of DE 196 13 941, Oct. 9, 1997.
English language Abstract of FR 2 863 167, dated Jun. 10, 2005.
English language Abstract of JP 2002-47144, dated Feb. 12, 2002.
English language Abstract of JP 2003-137756, dated May 14, 2003.
English language Abstract of WO 02/30369, dated Apr. 18, 2002.
English language Derwent Abstract of JP 2-19576, dated Jan. 23, 1990.
European Search Report for EP 06 29 0314 dated May 10, 2006, Examiner J. P. Fischer.
European Search Report for EP 06 29 0315, dated May 8, 2006, Examiner J. P. Fischer.
European Search Report for EP 06 29 0316, dated May 8, 2006, Examiner J. P. Fischer.
French Search Report for FR 05/02028 for U.S. Application No. 11/362,790 dated Nov. 1, 2005, Examiner J.P. Fischer.
French Search Report for FR 05/02029 for U.S. Appl. No. 11/362,787 dated Nov. 1, 2005, Examiner J.P. Fischer.
French Search Report for FR 05/02032 for U.S. Appl. No. 11/362,791 dated Nov. 1, 2005, Examiner J.P. Fischer.
Office Action mailed Apr. 27, 2009, in co-pending U.S. Appl. No. 11/795,640, Examiner E. Elhilo.
Office Action mailed Dec. 19, 2009, in co-pending U.S. Appl. No. 11/362,790, Examiner A. Khan.
Office Action mailed Feb. 13, 2008, in co-pending U.S. Appl. No. 11/362,790, Examiner R. Chung.
Office Action mailed Feb. 21, 2008, in co-pending U.S. Appl. No. 11/362,791, Examiner R. Chung.
Office Action mailed Feb. 6, 2008, in co-pending U.S. Appl. No. 11/362,787, Examiner R. Chung.
Office Action mailed Jul. 13, 2009 in co-pending U.S. Appl. No. 11/362,790, Examiner A. Khan.
Office Action mailed Jul. 22, 2009 in co-pending U.S. Appl. No. 11/362,787, Examiner A. Khan.
Office Action mailed Oct. 1, 2008 in co-pending U.S. Appl. No. 11/362,787, Examiner A. Khan.
Office Action mailed Oct. 2, 2008 in co-pending U.S. Appl. No. 11/362,791, Examiner A. Khan.
Zviak, C., The Science of Hair Care, pp. 215 and 278 (1986).

* cited by examiner

DYEING OF IN PARTICULAR HUMAN KERATIN MATERIALS BY DRY THERMAL TRANSFER OF A DIRECT ANTHRAQUINONE DYE, COMPOSITION COMPRISING THE SAID DYE AND ITS METHOD OF PREPARATION

CROSS-REFERENCE TO RELATED APPLICATIONS

This application is a national phase application of International Application No. PCT/EP2006/003296, filed Feb. 28, 2006, and claims the priority of French Application No. 0502030, filed Feb. 28, 2005, and the benefit of U.S. Provisional Application No. 60/681,456, filed May 17, 2005, the content of all of which is incorporated herein by reference.

The subject of the present invention is the use, for dyeing in particular human keratin materials, of a specific direct anthraquinone dye by dry thermal transfer. Its subject is furthermore a method for dyeing keratin materials in which a dry solid composition comprising the said direct anthraquinone dye is used. It relates furthermore to the composition and its method of preparation.

The invention relates more particularly to the field of dyeing human keratin fibres, and in particular hair.

It has been known for a long time to modify the colour of hair, and in particular to mask grey hair.

Essentially two types of technology are known which are used to dye human keratin fibres.

The first method, called direct or semipermanent dyeing, consists in changing or providing colour by the application of a coloured molecule which penetrates by diffusion into the fibre and/or remains adsorbed at its surface.

The second method, called oxidation dyeing or permanent dyeing, consists in changing or providing colour using, on the very inside of the fibre, an oxidative condensation of dye precursors which are weakly coloured or colourless compounds. After this reaction, the dyes formed are insoluble and are trapped inside the fibre.

The two methods summarized above make it possible to obtain numerous colours.

On the other hand, these methods are used with liquid compositions, which has the consequence of making these methods "messy" for clothes, hairdressing accessories (combs, towels and the like), tubs and the like.

Moreover, the dyeing times are generally long because the time for rinsing the product and the time for drying the hair should be added to the leave-in time for the composition.

Finally, the use of some dyes offering good dyeing performance on the fibres is sometimes limited because of their low solubility in liquid formulation carriers.

As can be seen, there is a constant search for methods for dyeing human keratin materials which, while allowing effective dyeing to be obtained, do not have the disadvantages mentioned above.

The subject of the present invention is therefore a method for dyeing keratin materials which make it possible to rapidly dye hair using dry thermal transfer of specific anthraquinone dyes, that is to say the passage from the solid state to the gaseous state without transition via the liquid state for these dyes.

This method has the advantage of not requiring the use of a liquid formulation carrier for the dye, which makes the dyeing particularly scarcely messy.

Furthermore, the fact that a liquid carrier is not required and that the dyes are used in a solid form makes it possible to use dyes which are sparingly soluble or which are unstable in conventional dyeing media. This can contribute to further broadening the pallet of colours possible.

Moreover, still by virtue of the fact that the dye is initially used in a solid form, there is no need either for rinsing, or for shampooing and/or for drying the materials treated.

Furthermore, thermal transfer being rapid, the leave-in times are short.

The latter two factors contribute to making the method according to the invention more rapid than conventional methods.

Finally, this method makes it possible to produce, in a simple manner, motifs on the materials treated, in particular on the hair.

Thus, the first subject of the present invention is the use of at least one direct anthraquinone dye of formula (I) which will be described in more detail below for dyeing in particular human keratin materials by dry thermal transfer.

Its subject is likewise a method for dyeing in particular human keratin materials, in which at least one direct anthraquinone dye of formula (I) contained in a dry composition is applied to or close to the keratin materials, and a source of heat is applied, causing the thermal transfer of the direct anthraquinone dye(s) at the surface and/or inside the keratin materials.

Its subject is furthermore a dry composition, in the form of a divided or undivided solid, comprising at least one anthraquinone dye of formula (I) and at least one film-forming polymer.

Finally, its subject is a method for preparing this composition, in which a mixture comprising at least one direct anthraquinone dye, at least one film-forming polymer and at least one solvent are applied to a support, and then the said solvent is evaporated.

However, other characteristics and advantages of the present invention will emerge more clearly on reading the description and the examples which follow.

In the text which follows, when it is specified that the composition is "dry", that means that the variation in the dry extract of such a composition, measured before and after a thermal treatment in an oven for one hour at 100° C., varies by 20% by weight or less, preferably by 10% by weight or less.

It is recalled that a solid compound is a compound which does not flow or does not undergo deformation when it is subjected to moderate forces. It should be noted that when the compound is in the form of a divided solid, the characteristics which have just been recalled apply at the level of the particle and not of a combination of particles deposited or otherwise on a support.

Moreover, the expression thermal transfer is understood to mean, for the purposes of the present invention, the application of heat to the dry composition brought into contact with the keratin materials to be treated or close to them. This heat is obtained by means of a source at a temperature more particularly between 100 and 500° C., advantageously between 130 and 250° C. and preferably between 140 and 220° C.

Preferably, this source of heat is brought into contact with the whole of the dry composition and keratin materials to be treated.

Without being bound by any theory, one of the possible mechanisms for dyeing keratin materials involves a step of vaporization or sublimation of the direct dye present in the dry composition according to the invention.

Human keratin materials denote more generally keratin fibres, such as hair or the eyelashes.

It should finally be recalled that, unless otherwise stated, the limits delimiting a range of values form part of this range.

As indicated above, this method according to the invention is carried out using at least one particular anthraquinone dye corresponding to the following formula (I):

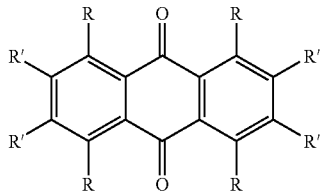

in which:

R, independently of each other, represent:
- a hydrogen atom;
- a hydroxyl group;
- an amino group;
- an amino group which is mono- or di-substituted with one or two radicals, which are identical or different, chosen from the radicals $C_1$-$C_6$ alkyl, $C_1$-$C_6$ hydroxyalkyl, $C_6$ aryl optionally substituted with one or more $C_1$-$C_6$ alkyl radicals;

R', independently of each other, represents:
- a hydrogen atom;
- a halogen atom;
- a hydroxyl group;
- an amino group;
- an amino group which is mono- or di-substituted with one or two radicals, which are identical or different, chosen from the radicals $C_1$-$C_6$ alkyl, $C_1$-$C_6$ alkylamino, $C_5$-$C_8$ cycloalkyl, ($C_1$-$C_6$)alkoxy($C_1$-$C_6$)alkyl;
- a $C_6$ aryl radical optionally substituted with one or more groups, which are identical or different, chosen from halogen atoms, the radicals $C_1$-$C_6$ alkyl, $C_1$-$C_6$ alkoxy, ($C_1$-$C_6$)alkoxy($C_1$-$C_6$)alkyl;
- a ($C_6$)aryloxy group;
- a ($C_6$)aryloxy group substituted with a ($C_6$)aryl-$SO_3$ group, the aryl group being optionally substituted with one or more groups, which are identical or different, chosen from halogen atoms, the groups hydroxyl, trifluoromethyl, $C_1$-$C_6$ alkyl, $C_1$-$C_6$ alkoxy, $C_6$ aryl, ($C_6$)aryl($C_1$-$C_4$)alkyl, ($C_6$)aryloxy, nitro, $C_2$-$C_6$ acyl, ($C_2$-$C_6$)acylamino, ($C_1$-$C_6$)alkylmercapto, $C_6$ thiophenyl, sulphonyloxy, ($C_1$-$C_6$)-alkylbenzenesulphonyl;
- a ($C_6$)aryloxy group substituted with a group —$SO_2N(R_a)_2$ with $R_a$, which are identical or different, representing a hydrogen atom, a radical $C_1$-$C_6$ alkyl, $C_2$-$C_6$ alkenyl, ($C_6$)aryl($C_1$-$C_6$)alkyl, $C_5$-$C_8$ cycloalkyl, it being possible for the two radicals $R_a$ to form, with the nitrogen atom to which they are attached, a 5- or 6-membered heterocycle;
- a group —$SR_b$ with $R_b$ representing a 5- or 6-membered heterocycle, comprising the sulphur atom and optionally comprising a nitrogen, sulphur or oxygen atom;
- —$COOR_c$ with $R_c$ representing a group $C_1$-$C_4$ hydroxyalkyl, ($C_1$-$C_4$)alkylphenyl, $C_5$-$C_8$ cycloalkyl, carbonyloxy($C_6$) aryl, carbonyl($C_6$) aryl;
- —$SO_3$—($C_6$)aryl, the aryl radical being optionally substituted with one or more groups, which are identical or different, chosen from halogen atoms, the groups hydroxyl, trifluoromethyl, $C_1$-$C_6$ alkyl, $C_1$-$C_6$ alkoxy, $C_6$ aryl, ($C_6$)aryl($C_1$-$C_4$)alkyl, ($C_6$)aryloxy, nitro, $C_2$-$C_6$ acyl, ($C_2$-$C_6$)acylamino, ($C_1$-$C_6$)alkylmercapto, thiophenyl, sulphonyloxy, ($C_1$-$C_6$)alkylbenzenesulphonyl.

Preferably, the direct anthraquinone dye corresponds to the following formula (Ia):

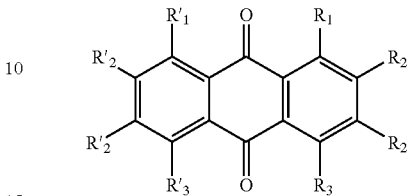

in which:

$R_1$ represents a hydrogen atom, a hydroxyl group, an amino group, an amino group which is mono- or di-substituted with one or two radicals, which are identical or different, chosen from the radicals $C_1$-$C_4$ alkyl, $C_1$-$C_6$ hydroxyalkyl, phenyl optionally substituted with one or more $C_1$-$C_4$ alkyl radicals;

$R'_1$ represents a hydrogen atom, a hydroxyl group, an amino group;

$R_2$, $R'_2$, independently of each other, represent
- a hydrogen atom;
- a halogen atom, preferably chlorine, bromine;
- a hydroxyl group;
- an amino group;
- an amino group which is mono- or di-substituted with one or two radicals, which are identical or different, chosen from the radicals $C_1$-$C_6$ alkyl, $C_1$-$C_6$ alkylamino, $C_5$-$C_8$ cycloalkyl, ($C_1$-$C_6$)alkoxy($C_1$-$C_6$)alkyl;
- a $C_6$ aryl radical optionally substituted with one or more groups, which are identical or different, chosen from halogen atoms, the radicals $C_1$-$C_6$ alkyl, $C_1$-$C_6$ alkoxy, ($C_1$-$C_6$)alkoxy($C_1$-$C_6$)alkyl;
- a ($C_6$)aryloxy group;

$R_3$ represents a hydrogen atom; a hydroxyl group; an amino group; an amino group which is mono- or di-substituted with one or two radicals, which are identical or different, chosen from the radicals $C_1$-$C_6$ alkyl, $C_1$-$C_6$ hydroxyalkyl, $C_6$ aryl optionally substituted with one or more $C_1$-$C_6$ alkyl radicals;

$R'_3$ represents a hydrogen atom; a hydroxyl group; an amino group.

Preferably, the direct dye used in the context of the present invention, and advantageously the direct azo dye, is chosen from compounds having an enthalpy of vaporization of less than or equal to 200 kJ/mol.

In accordance with an advantageous embodiment of the invention, the direct anthraquinone dye is chosen from the following direct dyes: Disperse Blue 1 [2475-45-8], Disperse Blue 3 [2475-46-9], Disperse Blue 14 [2475-44-7], Disperse Blue 19 [4395-65-7], Disperse Blue 26 [3860-63-7], Disperse Blue 56 [31810-89-6], Disperse Orange 11 [82-28-0], Disperse Red 60 [17418-58-5], Disperse Violet 1 [128-95-0], Solvent Blue 35 [17354-14-2], Solvent Blue 59 [6994-46-3], Solvent Green 3 [17418-58-5], 6-methyl-1,3,8-trihydroxyanthraquinone (Emodin) [518-82-1], Purpurin [81-54-9], quinalizarin [81-61-8], and mixtures thereof.

The method according to the invention therefore consists in applying at least one direct anthraquinone dye, contained in a dry composition, to or close to keratin materials, and in applying a source of heat causing thermal transfer of the direct dye(s) at the surface and/or inside the keratin materials. Preferably, the direct dye is applied to the keratin materials to be treated.

According to a first embodiment, the direct anthraquinone dye is applied to the keratin materials in the form of a divided solid, in free form. The expression free form is understood to mean that the direct azo dye does not exist in a form dispersed in a matrix.

According to one variant of this first embodiment, the direct dye is deposited in free form on a heat-resistant support. The keratin material, preferably hair, is applied to this support and the whole is heated by means of an instrument which releases heat. For example, a smoothing iron or a laser may be used.

According to a second embodiment of the invention, the direct dye is applied to the keratin materials in a divided solid form, in a non-free form. The direct dye is said to be in a non-free form when it is dispersed in a matrix. Advantageously, the direct dye is applied in the form of a film deposited or not deposited on a support.

In the case of this embodiment, the film comprises at least one film-forming polymer.

The period for which the heat source is applied is such that the keratin material is not substantially degraded. More particularly, the physical and physicochemical properties of the keratin material are not substantially impaired. There is furthermore no substantial modification of their natural colour, or modification of their mechanical resistance properties.

Thus, the higher the temperature, the shorter the duration of treatment.

By way of illustration, the duration is between 1 picosecond and 10 minutes.

The heat source may be provided in a conventional manner, such as for example a hair dryer, a hair dressing hood, a smoothing iron, a curling iron, a pulsed or non-pulsed laser system (a high-energy UV, visible or infrared light radiation), a heating tong system, and the like.

According to the method of the invention, a quantity of at least 0.0001 g of dye is deposited, by application, per gram of keratin material when it is in free form.

Furthermore, a quantity of at most 20 g of dye is deposited per gram of keratin material, more particularly at most 10 g of dye per gram of keratin material, and preferably at most 5 g of dye per gram of keratin material when it is in free form.

Advantageously, the keratin materials to which the film comprising the direct dye(s) is deposited are enclosed in a support which is resistant to heat under the application conditions. Furthermore, the support is aluminium foil, greaseproof paper or alternatively any synthetic material with a high glass transition temperature.

The operation may be carried out lock by lock or on the whole of the fibres.

Another subject of the present invention consists of a dry composition, preferably in the form of a film, comprising at least one direct anthraquinone dye, preferably in a state dispersed in the composition, of formula (I) mentioned above, and at least one film-forming polymer.

More particularly, the composition is provided in the form of a film deposited or not deposited on an appropriate support.

All the film-forming polymers are suitable for carrying out the invention, as long as they can be deposited by coating and remain cohesive once the film has been obtained and dried.

By way of examples of such film-forming polymers, reference may be made in particular to the manual International Cosmetic Ingredient Directory and Handbook 2000 edition, Volume 2, pages 1744 to 1747 which relates to film-forming compounds.

Among the polymers capable of entering into the composition of the films comprising the direct anthraquinone dye, there may be mentioned, for example, the polymers derived from vinylpyrrolidone, polyvinyl alcohol, polyurethanes, polymers derived from caprolactam, vinyllactam, vinyl acetate, polymers derived from acrylamide, polysaccharides capable of forming a film in the dry state such as cellulose derivatives, starches and derivatives, pullulan gum, gum arabic, pectins, alginates, carrageenans, galactomannans, agars, chitosans, chitins, polymers derived from hyaluronic acid, xanthan gum, karaya gum, proteins capable of forming a film in the dry state, such as gelatin, gluten, casein, zein, gliadin, hordein and their natural or synthetic derivatives, polymers derived from silicones, amphoteric or anionic polymers which are derived from monomers comprising at least one carboxylic, sulphonic or phosphoric functional group, acrylic copolymers of phosphorylcholine (lipidure), anion-cation complexes of the gum arabic/gelatin or gum arabic/chitosan type, or the collagen/GlycosAminoGlycan combination.

By way of suitable cationic film-forming polymers, there may be mentioned more particularly the following polymers, having in general a number-average molecular mass of between 500 and about 5 000 000:

(1) the homopolymers or copolymers derived from acrylic or methacrylic esters or amides and comprising at least one of the units of the following formula:

(A)

(B)

(C)

in which:

R$_1$ and R$_2$, which are identical or different, each represent a hydrogen atom or an alkyl group having from 1 to 6 carbon atoms;

R$_3$ denotes a hydrogen atom or a CH$_3$ group;

A is a linear or branched alkyl group of 1 to 6 carbon atoms, or a hydroxyalkyl group of 1 to 4 carbon atoms;

R$_4$, R$_5$, R$_6$, which are identical or different, represent an alkyl group having from 1 to 18 carbon atoms or a benzyl group;

X denotes a methosulphate anion or a halide such as chloride or bromide;

(2) the quaternized guar gums;

(3) the quaternized copolymers of vinylpyrrolidone and vinylimidazole;

(4) the chitosans or their salts;

the salts which can be used are in particular the acetate, lactate, glutamate, gluconate or pyrrolidonecarboxylate of chitosan.

The copolymers of the family (1) contain, in addition, one or more units derived from comonomers which may be chosen from the family of acrylamides, methacrylamides, diacetone acrylamides, acrylamides and methacrylamides substituted on the nitrogen with lower (C$_{1-4}$) alkyls, groups derived from acrylic or methacrylic acids or esters thereof, vinyllactams such as vinylpyrrolidone or vinylcaprolactam, vinyl esters.

Thus, among these copolymers of the family (1), there may be mentioned:

the copolymers of acrylamide and dimethylaminoethyl methacrylate quaternized with dimethyl sulphate or with a dimethyl halide, the copolymers of acrylamide and methacryloyloxyethyl-trimethylammonium chloride described, for example, in Patent Application EP-A-080976, the copolymers of acrylamide and methacryloyloxyethyl-trimethylammonium methosulphate, the vinylpyrrolidone/dialkylaminoalkyl acrylate or methacrylate copolymers, quaternized or otherwise, such as the products sold under the name "GAFQUAT®" by the company ISP such as for example "GAFQUAT® 734" or "GAFQUAT® 755" or alternatively the products called "COPOLYMER® 845, 958 and 937". These polymers are described in detail in French Patents 2 077 143 and 2 393 573, the dimethylaminoethyl methacrylate/vinylcaprolactam/vinylpyrrolidone terpolymers such as the product sold under the name GAFFIX® VC 713 by the company ISP, and the quaternized vinylpyrrolidone/dimethylaminopropyl methacrylamide copolymer such as in particular the product sold under the name "GAFQUAT® HS 100" by the company ISP.

Among these compounds, there may be mentioned chitosan having a degree of deacetylation of 90% by weight, pyrrolidone-chitosan carboxylate sold under the name KYTAMER® PC by the company AMERCHOL.

As regards the anionic film-forming polymers, the latter generally comprise at least one group derived from a carboxylic, sulphonic or phosphoric acid and have a number-average molecular mass of between about 500 and 5 000 000.

The carboxylic groups are more particularly provided by unsaturated mono- or dicarboxylic acid monomers such as those corresponding to the formula:

$$\underset{Rb}{\overset{Ra}{\diagdown}}C=C\underset{Rc}{\overset{(A_1)_n-COOH}{\diagup}}$$

in which n is an integer from 0 to 10, A$_1$ denotes a methylene group, optionally linked to the carbon atom of the unsaturated group or to the neighbouring methylene group, when n is greater than 1, through a heteroatom such as oxygen or sulphur, Ra denotes a hydrogen atom, or a phenyl or benzyl group, Rb denotes a hydrogen atom, a C$_1$-C$_4$ alkyl group, in particular methyl, ethyl or carboxyl, Rc denotes a hydrogen atom or a lower alkyl group, a group —CH$_2$—COOH, or a phenyl or benzyl group.

The preferred anionic film-forming polymers with carboxylic groups are:

A) the homo- or copolymers of acrylic or methacrylic acid or their salts and in particular the products sold under the names VERSICOL® E or K by the company ALLIED COLLOID and ULTRAHOLD® by the company BASF, the copolymers of acrylic acid and of acrylamide, the sodium salts of the polyhydroxycarboxylic acids.

B) The copolymers of acrylic or methacrylic acid with a monoethylene monomer such as ethylene, styrene, vinyl esters, acrylic or methacrylic acid esters, optionally grafted onto a polyalkylene glycol such as polyethylene glycol and optionally crosslinked. Such polymers are described in particular in French Patent 1 222 944 and German Application 2 330 956, copolymers of this type containing in their chain an acrylamide unit optionally N-alkylated and/or hydroxyalkylated as described especially in Luxembourg Patent Applications 75370 and 75371. There may also be mentioned the copolymers of acrylic acid and C$_1$-C$_4$ alkyl methacrylate and the terpolymers of vinylpyrrolidone, acrylic acid and C$_1$-C$_{20}$ alkyl, for example lauryl, methacrylate such as that sold by the company ISP under the name ACRYLIDONE® LM and the methacrylic acid/ethyl acrylate/tert-butyl acrylate terpolymers such as the product sold under the name LUVIMER® 100 P by the company BASF.

C) The copolymers derived from crotonic acid such as those containing in their chain vinyl propionate or acetate units and optionally other monomers such as methallyl or allyl esters, vinyl ether or vinyl ester of a linear or branched saturated carboxylic acid with a long hydrocarbon chain such as those containing at least 5 carbon atoms, it being possible for these polymers to be optionally grafted and crosslinked or alternatively another monomer which is a vinyl, allyl or methallyl ester of an α- or β-cyclic carboxylic acid. Such polymers are described, inter alia, in French Patents 1 222 944, 1 580 545, 2 265 782, 2 265 781, 1 564 110 and 2 439 798. A commercial product entering into this class is the resin 28-29-30 sold by the company NATIONAL STARCH.

D) The copolymers derived from C$_4$-C$_8$ monounsaturated carboxylic acids or anhydrides chosen from:

the copolymers comprising (i) one or more itaconic, fumaric or maleic acids or anhydrides and (ii) at least one monomer chosen from vinyl esters, vinyl ethers, vinyl halides, phenylvinyl derivatives, acrylic acid and its esters, the anhydride functions of these copolymers being optionally monoesterified or monoamidated. Such polymers are described in particular in patents U.S. Pat. Nos. 2,047,398, 2,723,248, 2,102,113 and Patent GB 839805. Marketed products are especially those sold under the names GANTREZ® AN or ES by the company ISP.

the copolymers comprising (i) one or more maleic, citraconic or itaconic anhydride units and (ii) one or more monomers chosen from allyl or methallyl esters optionally containing one or more acrylamide, methacrylamide or α-olefin groups, acrylic or methacrylic esters, acrylic or methacrylic acid or vinylpyrrolidone in their chain, the anhydride functions of these copolymers being optionally monoesterified or monoamidated.

These polymers are, for example, described in French Patents 2 350 384 and 2 357 241 by the applicant.

E) The polyacrylamides containing carboxylate groups;

F) the anionic polyurethanes, such as the product sold by BASF under the name Luviset PUR.

The polymers comprising sulphonic groups are polymers containing vinylsulphonic, styrenesulphonic, naphthalenesulphonic or acrylamidoalkylsulphonic units.

These polymers may be especially chosen from:

the salts of polyvinylsulphonic acid having a molecular mass of between about 1000 and 100 000 as well as the copolymers with an unsaturated comonomer such as acrylic or methacrylic acids and their esters as well as acrylamide or its derivatives, vinyl ethers and vinylpyrrolidone.

the salts of polystyrenesulphonic acid such as the sodium salts sold for example under the name Flexan® 130 by NATIONAL STARCH. These compounds are described in Patent FR 2 198 719.

the salts of polyacrylamidesulphonic acids, such as those mentioned in patent U.S. Pat. No. 4,128,631 and more particularly polyacrylamidoethylpropanesulphonic acid.

According to the invention, it is also possible to use film-forming anionic polymers of the grafted silicone type comprising a polysiloxane portion and a portion consisting of a nonsilicone organic chain, one of the two portions constituting the principal chain of the polymer, the other being grafted onto the said principal chain. These polymers are for example described in patent applications EP-A-0 412 704, EP-A-0 412 707, EP-A-0 640 105 and WO 95/00578, EP-A-0 582 152 and WO 93/23009 and patents U.S. Pat. No. 4,693,935, U.S. Pat. No. 4,728,571 and U.S. Pat. No. 4,972,037.

Such polymers are, for example, the copolymers which can be obtained by free-radical polymerization starting with a mixture of monomers, consisting of:

a) 50 to 90% by weight of tert-butyl acrylate;
b) 0 to 40% by weight of acrylic acid;
c) 5 to 40% by weight of silicone-containing macromer of formula:

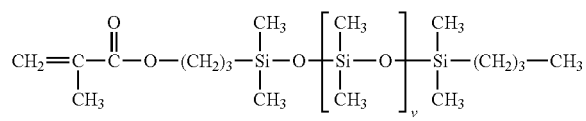

with v being a number ranging from 5 to 700; the percentages by weight being calculated relative to the total weight of the monomers.

Further examples of grafted silicone polymers include in particular polydimethylsiloxanes (PDMS) onto which are grafted, via a chain link of thiopropylene type, mixed polymer units of poly(meth)acrylic acid type or of poly(alkyl (meth) acrylate) type, and polydimethylsiloxanes (PDMS) onto which are grafted, via a chain link of thiopropylene type, polymer units of poly(isobutyl(meth)acrylate) type.

It is also possible use, as film-forming polymers, functionalized polyurethanes, containing silicone or not.

The polyurethanes particularly sought by the present invention are those described in patents EP 0 751 162, EP 0 637 600, FR 2 743 297 and EP 0 648 485 and the patents EP 0 656 021 or WO 94/03510 and EP 0 619 111.

According to the invention, the anionic film-forming polymers are preferably chosen from the acrylic acid copolymers such as the acrylic acid/ethyl acrylate/N-tert-butylacrylamide terpolymers sold under the name ULTRAHOLD® STRONG by the company BASF, the copolymers derived from crotonic acid such as the vinyl acetate/vinyl tert-butylbenzoate/crotonic acid terpolymers and the crotonic acid/vinyl acetate/vinyl neododecanoate terpolymers sold in particular under the name Résine 28-29-30 by the company NATIONAL STARCH, the polymers derived from itaconic, fumaric and maleic acids or anhydrides with vinyl esters, vinyl ethers, vinyl halides, phenylvinyl derivatives, acrylic acid and its esters such as the monoesterified maleic anhydride/methyl vinyl ether copolymers sold, for example, under the name GANTREZ® by the company ISP, the copolymers of methacrylic acid and of methyl methacrylate sold under the name EUDRAGIT® L by the company ROHM PHARMA, the copolymers of methacrylic acid and of ethyl acrylate sold under the name LUVIMER® MAEX or MAE by the company BASF and the vinyl acetate/crotonic acid copolymers and the vinyl acetate/crotonic acid copolymers grafted with polyethylene glycol sold under the name ARISTOFLEX® A by the company BASF and the polyurethane Luviset PUR® sold by the company BASF.

The anionic film-forming polymers which are most particularly preferred are those chosen from the monoesterified maleic anhydride/methyl vinyl ether copolymers sold under the name GANTREZ® ES 425 by the company ISP, the acrylic acid/ethyl acrylate/N-tert-butylacrylamide terpolymers sold under the name ULTRAHOLD® STRONG by the company BASF, the copolymers of methacrylic acid and of methyl methacrylate sold under the name EUDRAGIT® L by the company ROHM PHARMA, the vinyl acetate/vinyl tert-butylbenzoate/crotonic acid terpolymers and the crotonic acid/vinyl acetate/vinyl neododecanoate terpolymers sold under the name Résine 28-29-30 by the company NATIONAL STARCH, the copolymers of methacrylic acid and ethyl acrylate sold under the name LUVIMER® MAEX or MAE by the company BASF, the vinylpyrrolidone/acrylic acid/lauryl methacrylate terpolymers sold under the name ACRYLIDONE® LM by the company ISP and the polyurethane Luviset PUR® sold by the company BASF.

Among the amphoteric film-forming polymers which can be used, there may be mentioned those containing B and C units distributed randomly in the polymer chain where B denotes a unit which is derived from a monomer containing at least one basic nitrogen atom and C denotes a unit which is derived from an acidic monomer containing one or more carboxylic or sulphonic groups or alternatively B and C may denote groups which are derived from zwitterionic monomers of carboxybetaines or of sulphobetaines;

B and C may also denote a cationic polymer chain containing primary, secondary, tertiary or quaternary amine groups, in which at least one of the amine groups carries a carboxylic or sulphonic group linked via a hydrocarbon group or alternatively B and C form part of a chain of a polymer with an α-dicarboxylic ethylene unit in which one of the carboxylic groups has been caused to react with a polyamine containing one or more primary or secondary amine groups.

The amphoteric film-forming polymers corresponding to the definition given above which are more particularly preferred are chosen from the following polymers:

(1) The polymers resulting from the copolymerization of a monomer derived from a vinyl compound carrying a carboxylic group such as more particularly acrylic acid, methacrylic acid, maleic acid, alpha-chloroacrylic acid, and of a basic monomer derived from a substituted vinyl compound containing at least one basic atom (preferably an amino functional group) such as more particularly dialkylaminoalkyl methacrylate and acrylate, dialkylaminoalkylmethacrylamide and -acrylamide. Such compounds are described in American U.S. Pat. No. 3,836,537. There may also be mentioned the sodium acrylate/acrylamidopropyltrimethylammonium chloride copolymer sold under the name POLYQUART KE 3033 by the company HENKEL.

The vinyl compound may also be a dialkyldiallylammonium salt such as diethyldiallylammonium chloride. The copolymers of acrylic acid and the latter monomer are offered under the names MERQUAT 280, MERQUAT 295 and MERQUAT PLUS 3330 by the company CALGON.

(2) The polymers containing units which are derived from:
    a) at least one monomer chosen from acrylamides or methacrylamides substituted on the nitrogen atom by an alkyl group,
    b) at least one acidic comonomer containing one or more reactive carboxylic groups, and
    c) at least one basic comonomer such as esters with primary, secondary, tertiary and quaternary amine substituents of acrylic and methacrylic acids and the product of quaternization of dimethylaminoethyl methacrylate with dimethyl or diethyl sulphate.

The N-substituted acrylamides or methacrylamides more particularly preferred are compounds whose alkyl groups contain from 2 to 12 carbon atoms and more particularly N-ethylacrylamide, N-tert-butylacrylamide, N-tert-octylacrylamide, N-octylacrylamide, N-decylacrylamide, N-dodecylacrylamide as well as the corresponding methacrylamides.

The acidic comonomers are chosen more particularly from acrylic, methacrylic, crotonic, itaconic, maleic and fumaric acids as well as the alkyl monoesters having 1 to 4 carbon atoms of maleic or fumaric anhydrides or acids.

The basic comonomers preferred are methacrylates of aminoethyl, butylaminoethyl, N,N'-dimethylaminoethyl, N-tert-butylaminoethyl.

Particularly used are the copolymers whose CTFA name (4th ed., 1991) is Octylacrylamide/acrylates/butyl-aminoethyl methacrylate copolymer such as the products sold under the name AMPHOMER® or LOVOCRYL® 47 by the company NATIONAL STARCH.

(3) The partially or completely acylated and crosslinked polyaminoamides derived from polyaminoamides of general formula:

(III)

in which $R_{10}$ represents a divalent group derived from a saturated dicarboxylic acid, a mono- or dicarboxylic aliphatic acid with ethylenic double bond, an ester of a lower alkanol having 1 to 6 carbon atoms of these acids or a group which is derived from the addition of any one of the said acids with a bis-primary or bis-secondary amine, and Z denotes a group which is derived from a bis-primary, mono- or bis-secondary polyalkylene-polyamine and preferably represents:

a) in the proportions of 60 to 100 mol %, the group

(IV)

where x=2 and p=2 or 3, or alternatively x=3 and p=2 this group being derived from diethylenetriamine, triethylenetetraamine or dipropylenetriamine;

b) in the proportions of 0 to 40 mol %, the group (IV) above, in which x=2 and p=1 and which is derived from ethylenediamine, or the group which is derived from piperazine:

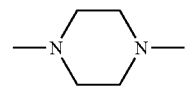

c) in the proportions of 0 to 20 mol %, the group —NH—$(CH_2)_6$—NH— which is derived from hexamethylenediamine, these polyamino amides being crosslinked by adding a bifunctional crosslinking agent chosen from the epihalohydrins, diepoxides, dianhydrides, bis-unsaturated derivatives, by means of 0.025 to 0.35 mol of crosslinking agent per amine group of the polyamino amide and acylated by the action of acrylic acid, chloroacetic acid or of an alkanesultone or of their salts.

The saturated carboxylic acids are preferably chosen from the acids having 6 to 10 carbon atoms such as adipic, 2,2,4-trimethyladipic and 2,4,4-trimethyladipic acids, terephthalic acid, the acids with ethylene double bond such as for example acrylic, methacrylic and itaconic acids.

The alkanesultones used in the acylation are preferably propane- or butanesultone, the salts of the acylating agents are preferably the sodium or potassium salts.

(4) The polymers containing zwitterionic units of formula:

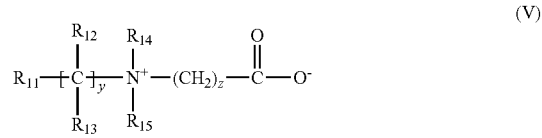
(V)

in which $R_{11}$ denotes a polymerizable unsaturated group such as an acrylate, methacrylate, acrylamide or methacrylamide group, y and z represent an integer from 1 to 3, $R_{12}$ and $R_{13}$ represent a hydrogen atom or a methyl, ethyl or propyl group, $R_{14}$ and $R_{15}$ represent a hydrogen atom or an alkyl group such that the sum of the carbon atoms in $R_{14}$ and $R_{15}$ does not exceed 10.

The polymers comprising such units may also comprise units derived from nonzwitterionic monomers such as dimethyl- or diethylaminoethyl acrylate or methacrylate or alkyl acrylates or methacrylates, acrylamides or methacrylamides or vinyl acetate.

By way of example, there may be mentioned the copolymers of methyl methacrylate/N,N-dimethyl-carboxyaminoethyl methacrylate.

(5) The polymers derived from chitosan containing monomeric units corresponding to the following formulae:

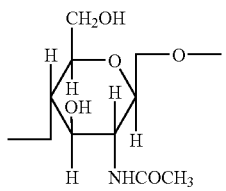
(D)

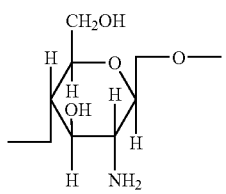
(E)

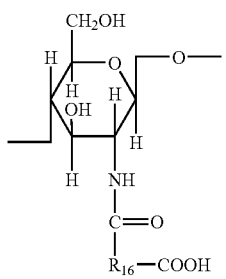
(F)

the (D) unit being present in proportions of between 0 and 30%, the (E) unit in proportions of between 5 and 50% and the (F) unit in proportions of between 30 and 90%, it being understood that in this (F) unit, $R_{16}$ represents a group of formula:

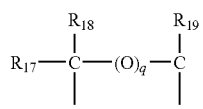

in which if q=0, $R_{17}$, $R_{18}$ and $R_{19}$, which are identical or different, each represent a hydrogen atom, a methyl, hydroxyl, acetoxy or amino residue, a monoalkylamine residue or a dialkylamine residue optionally interrupted by one or more nitrogen atoms and/or optionally substituted with one or more amine, hydroxyl, carboxyl, alkylthio or sulphonic groups, or an alkylthio residue whose alkyl group carries an amino residue, at least one of the $R_{17}$, $R_{18}$ and $R_{19}$ groups being in this case a hydrogen atom;

or if q=1, $R_{17}$, $R_{18}$ and $R_{19}$ each represent a hydrogen atom, as well as the salts formed by these compounds with bases or acids.

(6) The polymers corresponding to the general formula (VI) are described for example in French Patent 1 400 366 and comprising the repeating unit below:

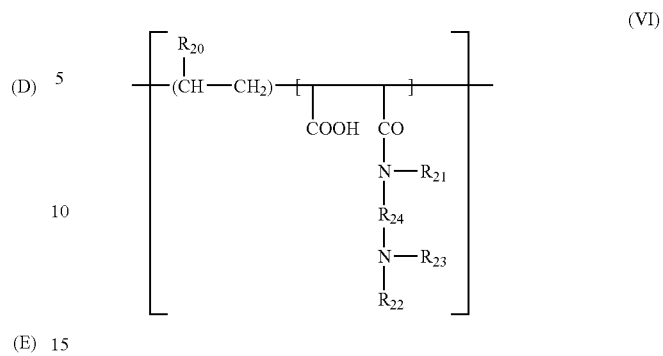
(VI)

in which $R_{20}$ represents a hydrogen atom, a $CH_3O$, $CH_3CH_2O$ or phenyl group, $R_{21}$ denotes a hydrogen atom or a lower alkyl group such as methyl or ethyl, $R_{22}$ denotes a hydrogen atom or a $C_1$-$C_6$ lower alkyl group such as methyl or ethyl, $R_{23}$ denotes a $C_3$-$C_6$ lower alkyl group such as methyl or ethyl or a group corresponding to the formula: —$R_{24}$—$N(R_{22})_2$, $R_{24}$ representing a group —$CH_2$—$CH_2$—, —$CH_2$—$CH_2$—$CH_2$— or —$CH_2$—$CH(CH_3)$—, $R_{22}$ having the meanings mentioned above.

(7) The polymers derived from the N-carboxyalkylation of chitosan such as N-carboxymethyl chitosan or N-carboxybutyl chitosan.

(8) The amphoteric polymers of the -D-X-D-X- type chosen from:

a) the polymers obtained by the action of chloroacetic acid or sodium chloroacetate on the compounds containing at least one unit of formula:

-D-X-D-X-D- (VII)

where D denotes a group

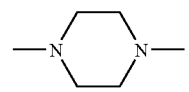

and X denotes the symbol E or E', E and E', which are identical or different, denote a bivalent group which is an alkylene group with a linear or branched chain containing up to 7 carbon atoms in the principal chain which is unsubstituted or substituted with hydroxyl groups and which may contain, in addition, oxygen, nitrogen or sulphur atoms, 1 to 3 aromatic and/or heterocyclic rings; the oxygen, nitrogen and sulphur atoms being present in the form of ether, thioether, sulphoxide, sulphone, sulphonium, alkylamine or alkenylamine groups, or hydroxyl, benzylamine, amine oxide, quaternary ammonium, amide, imide, alcohol, ester and/or urethane groups.

b) The polymers of formula:

-D-X-D-X- (VII')

where D denotes a group

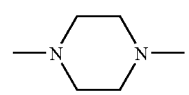

and X denotes the symbol E or E' and, at least once, E'; E having the meaning indicated above and E' is a bivalent group which is an alkylene group with a linear or branched chain having up to 7 carbon atoms in the principal chain, which is unsubstituted or substituted with one or more hydroxyl groups and containing one or more nitrogen atoms, the nitrogen atom being substituted with an alkyl chain optionally interrupted by an oxygen atom and necessarily containing one or more carboxyl functional groups or one or more hydroxyl functional groups and betainized by reaction with chloroacetic acid or sodium chloroacetate.

(9) The ($C_1$-$C_5$)alkyl vinyl ether/maleic anhydride copolymers partially modified by semiamidation with an N,N-dialkylaminoalkylamine such as N,N-dimethylaminopropylamine or by semiesterification with an N,N-dialkylaminoalkanol. These copolymers may also contain other vinyl comonomers such as vinylcaprolactam.

The preferred amphoteric film-forming polymers are those of the family (3) such as the copolymers whose CTFA name is Octylacrylamide/acrylates/butylaminoethyl methacrylate copolymer such as the products sold under the names AMPHOMER®, AMPHOMER® LV 71 or LOVOCRYL® 47 by the company NATIONAL STARCH and those of the family (4) such as the butyl methacrylate/N,N-dimethylcarboxyaminoethyl methacrylate copolymers.

The nonionic film-forming polymers which can be used according to the present invention are chosen for example from:
the homopolymers of vinyl acetate;
the copolymers of vinyl acetate and acrylic ester;
the copolymers of vinyl acetate and ethylene;
the copolymers of vinyl acetate and maleic ester, for example dibutyl maleate;
the copolymers of acrylic esters such as for example the copolymers of alkyl acrylates and alkyl methacrylates such as the products offered by the company ROHM & HAAS under the names PRIMAL® AC-261 K and EUDRAGIT® NE 30 D, by the company BASF under the name 8845, by the company HOECHST under the name APPRETAN® N9212;
the copolymers of acrylonitrile and of a nonionic monomer chosen for example from butadiene and alkyl (meth) acrylates; there may be mentioned the products offered under the name CJ 0601 B by the company ROHM & HAAS;
the homopolymers of styrene;
the copolymers of styrene and alkyl (meth)acrylate such as the products MOWILITH® LDM 6911, MOWILITH® DM 611 and MOWILITH® LDM 6070 offered by the company HOECHST, the products RHODOPAS® SD 215 and RHODOPAS® DS 910 offered by the company RHODIA CHIMIE;
the copolymers of styrene, alkyl methacrylate and alkyl acrylate;
the nonionic polyurethanes;
the copolymers of styrene and butadiene;
the copolymers of styrene, butadiene and vinylpyridine;
the copolymers of alkyl acrylate and urethane;
the polyamides;
the homopolymers and copolymers of vinyllactam.

The alkyl groups of the nonionic polymers mentioned above preferably have from 1 to 6 carbon atoms.

According to the present invention, the film-forming polymers are preferably nonionic polymers, and better still nonionic polymers with vinyllactam units. They are described in particular in patents U.S. Pat. No. 3,770,683, U.S. Pat. No. 3,929,735, U.S. Pat. No. 4,521,504, U.S. Pat. No. 5,158,762, U.S. Pat. No. 5,506,315 and in Patent Applications WO 94/121148, WO 96/06592 and WO 96/10593. They may be provided in pulverulent form or in the form of a solution or a suspension.

The homopolymers or copolymers with vinyllactam units comprise units of formula:

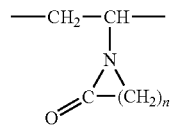

in which n is independently 3, 4 or 5.

The number-average molecular mass of the polymers with vinyllactam units is generally greater than about 5000, preferably between 10 000 and 1 000 000 approximately, more preferably between 10 000 and 100 000 approximately.

It is possible to use, in particular, as film-forming polymer, in the present invention, polyvinyl-pyrrolidones such as those marketed under the name Luviskol® K30 by the company BASF; polyvinylcaprolactams such as those marketed under the name Luviskol® PLUS by the company BASF; poly (vinylpyrrolidone/vinyl acetate) copolymers such as those marketed under the name PVPVA® S630L by the company ISP, Luviskol® VA 73, VA 64, VA 55, VA 37 and VA 28 by the company BASF; and poly(vinylpyrrolidone/vinyl acetate/vinyl propionate) terpolymers such as for example those marketed under the name Luviskol® VAP 343 by the company BASF.

According to this second embodiment, the composition, in film form, may comprise at least one plasticizer.

The plasticizers conventionally used in the field may be used in the composition.

However, by way of more specific examples, there may be mentioned, inter alia, urea, glycerine, sorbitol, mono- and/or disaccharides, dipropylene glycol, butylene glycol, pentylene glycol or polyethylene glycol, benzyl alcohol, or mixtures thereof.

Advantageously, the film may contain at least one formulation adjuvant and/or cosmetic active agent chosen for example from dispersing agents such as alkali metal lignosulphonates, antioxidants, pH-regulating agents, perfumes, silicones, ceramides.

Usually, the content of adjuvant in the composition represents, for each, from 0.01 to 20% each; the total content of additives, if they are present, not exceeding 80% by weight of the dry solid composition.

The composition according to the invention may additionally be in the form of a film deposited or not deposited on a support.

If the support is present, the latter is advantageously chosen from compounds which are not degraded under the conditions for carrying out the method.

The support is chosen from compounds which do not become solubilized under the conditions for preparing the said film. Thus, the support is not soluble in an aqueous medium.

Furthermore, the support may be chosen from compounds which conduct electricity or from compounds which are electrical insulators.

The water-soluble or water-insoluble support may thus be made of a material chosen from polyurethanes, thermoplastic elastomers of the type including styrene-butadiene-styrene, styrene-ethylene-butadiene-styrene, ethylene-vinyl acetate, or coether ester, polyethylenes, polypropylenes, or silicones.

Such supports are sold in particular under the trade marks: BAYDUR®, DALTOFLEX®, UROFLEX®, HYPERLAST®, INSPIRE®, DESMOPAN®, ESTANE®, LASTANE®, TEXIN®, CARIFLEX®, KRATON®, SOLPRENE®, ELVAX®, ESCORENE®, OPTENE®, ARNITEL®, HYTREL®, or RITEFLEX®.

It would not be excluded to choose, as support, an inorganic compound such as for example aluminium.

It is specified that the thickness of the support on which the composition is deposited preferably has a thickness which allows easy use for dyeing the keratin materials (easy folding, sufficient solidity to allow several applications with several foldings and unfoldings).

Usually, the thickness of the support is preferably between 0.01 mm and 2 mm, and preferably between 0.02 and 0.2 mm.

Furthermore, when the composition is deposited on a support, the thickness of the film made of the composition is usually between 20 µm and 1000 µm, and preferably between 50 µm and 200 µm.

In the case where the composition is in the form of a film not deposited on a support, the thickness of the film made of the composition is close to 0.01 mm to 2 mm, preferably 0.02 to 0.2 mm.

Another subject of the invention consists of a method for preparing a composition in the form of a film.

More particularly, a method consists in carrying out the following steps:

a) a composition comprising at least one dye of formula (I), at least one film-forming polymer and at least one solvent is prepared;
b) a film made of the composition thus obtained is deposited on an appropriate support;
c) the solvent is evaporated.

The solvent entering into the composition is chosen from the compounds which solubilize or disperse at least the film-forming polymer. In the latter case, the film-forming polymers are in the form of dispersions of solid or liquid particles of polymer (latex or pseudolatex).

Moreover, the solvent furthermore has a boiling point less than the sublimation temperature of the dye and less than the degradation temperature of the film-forming polymer. Advantageously, the boiling point of the solvent is less than or equal to 110° C.

By way of examples of solvents which can be used, there may be mentioned for example water, ethanol, acetone, isopropanol, ethyl acetate, dichloromethane, ethyl ether and the like.

Preferably, the composition comprises from 5 to 99.9% by weight of solvent.

It should be noted, advantageously, that the composition comprises from 0.0001 to 60% of direct anthraquinone dye.

Moreover, according to a particular embodiment, the composition comprises from 0.01 to 80% by weight of film-forming polymer.

Once the composition has been obtained, it is deposited on an appropriate support, such as for example a non-rough and horizontal support of the heating or non-heating bed or marble type.

It should be specified that, advantageously, the composition is deposited directly on the support with which the composition is intended to be used for dyeing, if such a variant is chosen.

It is preferable for the thickness of the composition deposited to be relatively uniform.

Furthermore, the thickness of the composition deposited is such that a film is obtained, preferably after evaporation of the solvent, which can be handled at room temperature (more particularly between 15 and 30° C.). Without limitation, the thickness of the composition deposited varies in general from 0.01 to 2 mm, preferably from 0.02 to 2 mm.

The composition is deposited in a conventional manner, without, but preferably with, an apparatus which makes it possible to obtain a substantially uniform film thickness.

After depositing the composition, the solvent is evaporated in a conventional manner.

The film obtained is then separated from its support and then deposited on the materials to be treated.

Concrete but nonlimiting examples of the invention will now be presented.

EXAMPLES

1. Preparation of a Dyed Film

The following mixture is prepared, with stirring for 20 minutes

| Constituent | Concentration |
|---|---|
| Dye | 2% |
| Hydroxypropylcellulose sold under the name Klucel MF by the company Aqualon | 1.5% |
| Ethanol | qs. 100% | and deposited on a heating plate at 60° C. The dyed film is formed by evaporation of the ethanol.

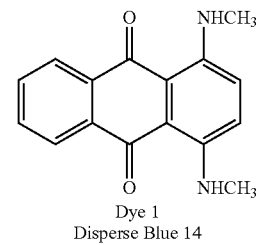

Dye 1
Disperse Blue 14

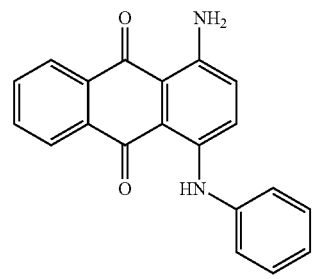

Dye 2
Disperse Blue 19

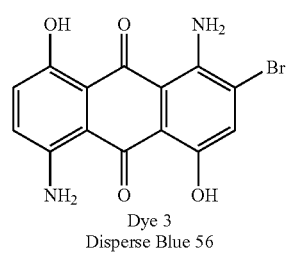

Dye 3
Disperse Blue 56

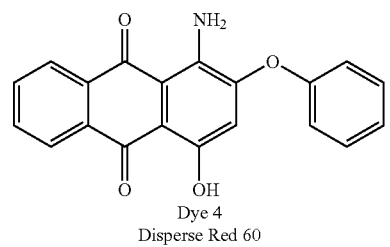
Dye 4
Disperse Red 60
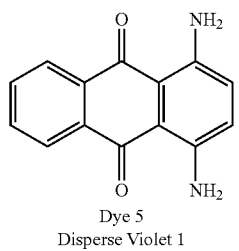
Dye 5
Disperse Violet 1
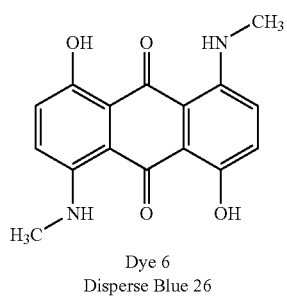
Dye 6
Disperse Blue 26
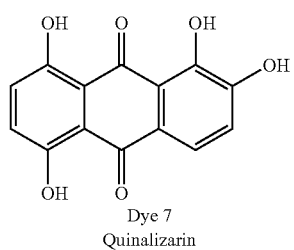
Dye 7
Quinalizarin
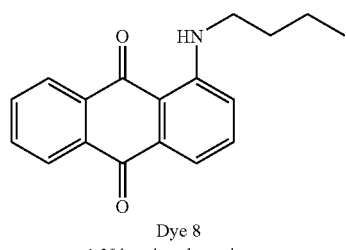
Dye 8
1-N,butyl-anthraquinone
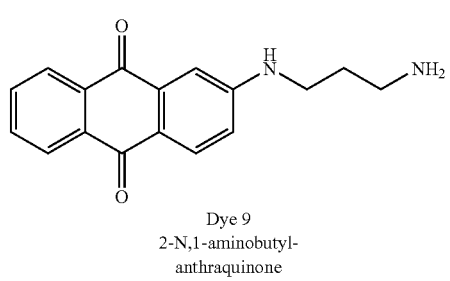
Dye 9
2-N,1-aminobutyl-
anthraquinone
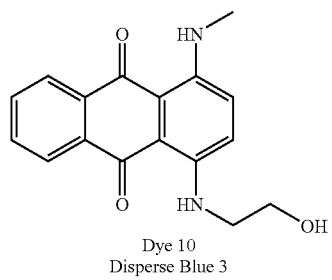
Dye 10
Disperse Blue 3
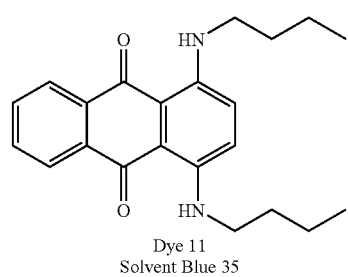
Dye 11
Solvent Blue 35
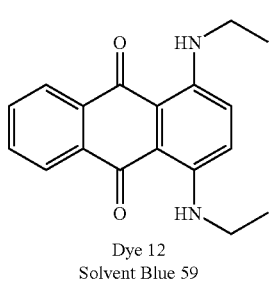
Dye 12
Solvent Blue 59
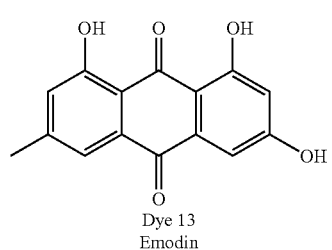
Dye 13
Emodin
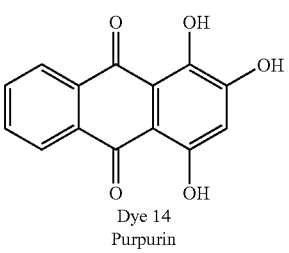
Dye 14
Purpurin
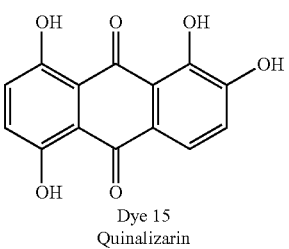
Dye 15
Quinalizarin 2. Hair Dyeing The film obtained above is applied to natural hair which is 90% white.

Each lock is then covered with aluminium foil.

Heat is applied by means of a Japanese smoothing iron Thermal Effect Iron (temperature and duration indicated in the table below).

At the end, the locks are dyed.

No rinsing is necessary.

The colour of each lock is then measured (Minolta CM3600d spectrocolorimeter, specular components included, angle 10°, illuminant D65).

3. Colorimetric Results

| Name | L* |
|---|---|
| Control | 61.3 |
| Dye 1 | 43.2 |
| Dye 2 | 46.5 |
| Dye 3 | 38.0 |
| Dye 4 | 39.5 |
| Dye 5 | 36.2 |
| Dye 6 | 35.1 |
| Dye 7 | 46.1 |
| Dye 8 | 42.0 |
| Dye 9 | 33.1 |
| Dye 10 | 34.4 |
| Dye 11 | 19.6 |
| Dye 12 | 39.1 |
| Dye 13 | 58.8 |
| Dye 14 | 40.6 |
| Dye 15 | 46.1 |

The invention claimed is:

1. A method for dyeing keratin materials comprising applying a dye composition to the keratin materials by dry thermal transfer, the dye composition comprising at least one direct anthraquinone dye of the following formula (I):

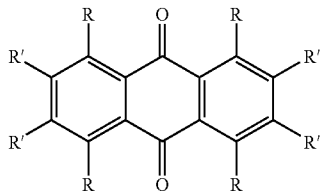

in which:
R, independently of each other, represent:
a hydrogen atom;
a hydroxyl group;
an amino group; or
an amino group which is mono- or di-substituted with one or two radicals, which are identical or different, chosen from the radicals $C_1$-$C_6$ alkyl, $C_1$-$C_6$ hydroxyalkyl, and $C_6$ aryl optionally substituted with one or more $C_1$-$C_6$ alkyl radicals; and
R', independently of each other, represent:
a hydrogen atom;
a halogen atom;
a hydroxyl group;
an amino group;
an amino group which is mono- or di-substituted with one or two radicals, which are identical or different, chosen from the radicals $C_1$-$C_6$ alkyl, $C_1$-$C_6$ alkylamino, $C_5$-$C_8$ cycloalkyl, and $(C_1$-$C_6)$alkoxy$(C_1$-$C_6)$alkyl;

a $C_6$ aryl radical optionally substituted with one or more groups, which are identical or different, chosen from halogen atoms and the radicals $C_1$-$C_6$ alkyl, $C_1$-$C_6$ alkoxy, and $(C_1$-$C_6)$alkoxy$(C_1$-$C_6)$alkyl;
a $(C_6)$aryloxy group;
a $(C_6)$aryloxy group substituted with a $(C_6)$aryl-$SO_3$ group, the aryl group being optionally substituted with one or more groups, which are identical or different, chosen from halogen atoms and the groups hydroxyl, trifluoromethyl, $C_1$-$C_6$ alkyl, $C_1$-$C_6$ alkoxy, $C_6$ aryl, $(C_6)$aryl$(C_1$-$C_4)$alkyl, $(C_6)$aryloxy, nitro, $C_2$-$C_6$ acyl, $(C_2$-$C_6)$ acylamino, $(C_1$-$C_6)$alkylmercapto, $C_6$ thiophenyl, sulfonyloxy, and $(C_1$-$C_6)$alkylbenzenesulfonyl;
a $(C_6)$aryloxy group substituted with a group —$SO_2N(R_a)_2$ with $R_a$, which are identical or different, representing a hydrogen atom, a radical $C_1$-$C_6$ alkyl, $C_2$-$C_6$ alkenyl, $(C_6)$aryl$(C_1$-$C_6)$alkyl, or $C_5$-$C_8$ cycloalkyl, it being possible for the two radicals $R_a$ to form, with the nitrogen atom to which they are attached, a 5-or 6-membered heterocycle;
a group —$SR_b$ with $R_b$ representing a 5-or 6-membered heterocycle, comprising the sulfur atom and optionally comprising a nitrogen, sulfur, or oxygen atom;
—$COOR_c$ with $R_c$ representing a group $C_1$-$C_4$ hydroxyalkyl, $(C_1$-$C_4)$alkylphenyl, $C_5$-$C_8$ cycloalkyl, carbonyloxy$(C_6)$aryl, or carbonyl$(C_6)$aryl; or
—$SO_3$—$(C_6)$aryl, the aryl radical being optionally substituted with one or more groups, which are identical or different, chosen from halogen atoms, the groups hydroxyl, trifluoromethyl, $C_1$-$C_6$ alkyl, $C_1$-$C_6$ alkoxy, $C_6$ aryl, $(C_6)$aryl$(C_1$-$C_4)$alkyl, $(C_6)$aryloxy, nitro, $C_2$-$C_6$ acyl, $(C_2$-$C_6)$acylamino, $(C_1$-$C_6)$alkylmercapto, thiophenyl, sulfonyloxy, and $(C_1$-$C_6)$alkylbenzenesulfonyl.

2. The method according to claim 1, wherein the at least one direct anthraquinone dye corresponds to the following formula (Ia):

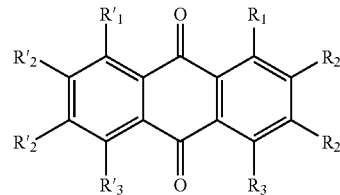

in which:
$R_1$ represents a hydrogen atom, a hydroxyl group, an amino group, or an amino group which is mono- or di-substituted with one or two radicals, which are identical or different, chosen from the radicals $C_1$-$C_4$ alkyl, $C_1$-$C_6$ hydroxyalkyl, and phenyl optionally substituted with one or more $C_1$-$C_4$ alkyl radicals;
$R'_1$ represents a hydrogen atom, a hydroxyl group, or an amino group;
$R_2$ and $R'_2$, independently of each other, represent
a hydrogen atom;
a halogen atom;
a hydroxyl group;
an amino group;
an amino group which is mono- or di-substituted with one or two radicals, which are identical or different, chosen from the radicals $C_1$-$C_6$ alkyl, $C_1$-$C_6$ alkylamino, $C_5$-$C_8$ cycloalkyl, and $(C_1$-$C_6)$alkoxy$(C_1$-$C_6)$alkyl;

a $C_6$ aryl radical optionally substituted with one or more groups, which are identical or different, chosen from halogen atoms, the radicals $C_1$-$C_6$ alkyl, $C_1$-$C_6$ alkoxy, and $(C_1$-$C_6)$alkoxy$(C_1$-$C_6)$alkyl; or a $(C_6)$aryloxy group;

$R_3$ represents a hydrogen atom; a hydroxyl group; an amino group; an amino group which is mono- or di-substituted with one or two radicals, which are identical or different, chosen from the radicals $C_1$-$C_6$ alkyl, $C_1$-$C_6$ hydroxyalkyl, and $C_6$ aryl optionally substituted with one or more $C_1$-$C_6$ alkyl radicals; and $R'_3$ represents a hydrogen atom; a hydroxyl group; or an amino group.

3. The method according to claim 1, wherein the keratin materials are human hair materials.

4. A method for dyeing human keratin materials, wherein a composition comprising at least one direct anthraquinone dye is applied to the human keratin materials, and a source of heat causing the sublimation of the at least one direct anthraquinone dye is applied, the at least one direct anthraquinone dye corresponding to the following formula (I):

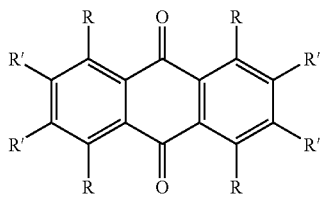

in which:
R, independently of each other, represent:
a hydrogen atom;
a hydroxyl group;
an amino group; or
an amino group which is mono- or di-substituted with one or two radicals, which are identical or different, chosen from the radicals $C_1$-$C_6$ alkyl, $C_1$-$C_6$ hydroxyalkyl, and $C_6$ aryl optionally substituted with one or more $C_1$-$C_6$ alkyl radicals; and R', independently of each other, represent:
a hydrogen atom;
a halogen atom;
a hydroxyl group;
an amino group;
an amino group which is mono- or di-substituted with one or two radicals, which are identical or different, chosen from the radicals $C_1$-$C_6$ alkyl, $C_1$-$C_6$ alkylamino, $C_5$-$C_8$ cycloalkyl, and $(C_1$-$C_6)$alkoxy$(C_1$-$C_6)$alkyl;

a $C_6$ aryl radical optionally substituted with one or more groups, which are identical or different, chosen from halogen atoms and the radicals $C_1$-$C_6$ alkyl, $C_1$-$C_6$ alkoxy, and $(C_1$-$C_6)$alkoxy$(C_1$-$C_6)$alkyl;

a $(C_6)$aryloxy group;

a $(C_6)$aryloxy group substituted with a $(C_6)$aryl-$SO_3$ group, the aryl group being optionally substituted with one or more groups, which are identical or different, chosen from halogen atoms and the groups hydroxyl, trifluoromethyl, $C_1$-$C_6$ alkyl, $C_1$-$C_6$ alkoxy, $C_6$ aryl, $(C_6)$aryl$(C_1$-$C_4)$alkyl, $(C_6)$aryloxy, nitro, $C_2$-$C_6$ acyl, $(C_2$-$C_6)$acylamino, $(C_1$-$C_6)$alkylmercapto, $C_6$ thiophenyl, sulfonyloxy, and $(C_1$-$C_6)$alkylbenzenesulfonyl;

a $(C_6)$aryloxy group substituted with a group —$SO_2N(R_a)_2$ with $R_a$, which are identical or different, representing a hydrogen atom, a radical $C_1$-$C_6$ alkyl, $C_2$-$C_6$ alkenyl, $(C_6)$aryl$(C_1$-$C_4)$alkyl, or $C_5$-$C_8$ cycloalkyl, it being possible for the two radicals $R_a$ to form, with the nitrogen atom to which they are attached, a 5-or 6-membered heterocycle;

a group —$SR_b$ with $R_b$ representing a 5-or 6-membered heterocycle, comprising the sulfur atom and optionally comprising a nitrogen, sulfur, or oxygen atom;

—$COOR_c$ with $R_c$ representing a group $C_1$-$C_4$ hydroxyalkyl, $(C_1$-$C_4)$alkylphenyl, $C_5$-$C_8$ cycloalkyl, carbonyloxy$(C_6)$aryl, or carbonyl$(C_6)$aryl; or —$SO_3$—$(C_6)$aryl, the aryl radical being optionally substituted with one or more groups, which are identical or different, chosen from halogen atoms and the groups hydroxyl, trifluoromethyl, $C_1$-$C_6$ alkyl, $C_1$-$C_6$ alkoxy, $C_6$ aryl, $(C_6)$aryl$(C_1$-$C_4)$ alkyl, $(C_6)$aryloxy, nitro, $C_2$-$C_6$, $(C_2$-$C_6)$acylamino, $(C_1$-$C_6)$alkylmercapto, thiophenyl, sulfonyloxy, and $(C_1$-$C_6)$alkylbenzenesulfonyl.

5. A method for dyeing human keratin materials, wherein a composition comprising at least one direct anthraquinone dye is applied to the human keratin materials and a source of heat causing the sublimation of the at least one direct anthraquinone dye is applied; the at least one direct anthraquinone dye corresponding to the following formula (Ia):

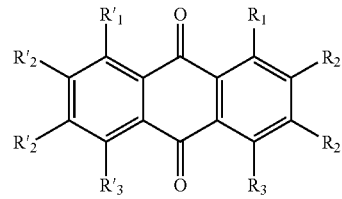

in which:
$R_1$ represents a hydrogen atom, a hydroxyl group, an amino group, an amino group which is mono- or di-substituted with one or two radicals, which are identical or different, chosen from the radicals $C_1$-$C_4$ alkyl, $C_1$-$C_6$ hydroxyalkyl, and phenyl optionally substituted with one or more $C_1$-$C_4$ alkyl radicals;

$R'_1$ represents a hydrogen atom, a hydroxyl group, or an amino group;

$R_2$ and $R'_2$, independently of each other, represent
a hydrogen atom;
a halogen atom;
a hydroxyl group;
an amino group;
an amino group which is mono- or di-substituted with one or two radicals, which are identical or different, chosen from the radicals $C_1$-$C_6$ alkyl, $C_1$-$C_6$ alkylamino, $C_5$-$C_8$ cycloalkyl, and $(C_1$-$C_6)$alkoxy$(C_1$-$C_6)$alkyl;

a $C_6$ aryl radical optionally substituted with one or more groups, which are identical or different, chosen from halogen atoms and the radicals $C_1$-$C_6$ alkyl, $C_1$-$C_6$ alkoxy, and $(C_1$-$C_6)$alkoxy$(C_1$-$C_6)$alkyl; or a $(C_6)$aryloxy group;

$R_3$ represents a hydrogen atom; a hydroxyl group; an amino group; an amino group which is mono- or di-substituted with one or two radicals, which are identical or different, chosen from the radicals $C_1$-$C_6$ alkyl, $C_1$-$C_6$ hydroxyalkyl, and $C_6$ aryl optionally substituted with one or more $C_1$-$C_6$ alkyl radicals; and R'$_3$ represents a hydrogen atom; a hydroxyl group; or an amino group.

6. The method according to claim 4, wherein the at least one direct anthraquinone dye is chosen from compounds having an enthalpy of evaporation less than or equal to 200 kJ/mol.

7. The method according to claim 4, wherein the at least one direct anthraquinone dye is chosen from Disperse Blue 1 [2475-45-8], Disperse Blue 3 [2475-46-9], Disperse Blue 14 [2475-44-7], Disperse Blue 19 [4395-65-7], Disperse Blue 26 [3860-63-7], Disperse Blue 56 [31810-89-6], Disperse Orange 11 [82-28-0], Disperse Red 60 [17418-58-5], Disperse Violet 1 [128-95-0], Solvent Blue 35 [17354-14-2], Solvent Blue 59 [6994-46-3], Solvent Green 3 [17418-58-5], 6-methyl-1,3,8-tri-hydroxyanthraquinone (Emodin) [518-82-1], purpurin [81-54-9], quinalizarin [81-61-8], and mixtures thereof.

8. The method according to claim 4, wherein the source of heat is at a temperature ranging from 100° C. to 500° C.

9. The method according to claim 4, wherein the duration of the method is such that the human keratin material is not substantially degraded.

10. The method according to claim 4, wherein the duration ranges from 1 picosecond to 10 minutes.

11. The method according to claim 4, wherein a quantity of at least 0.0001 g of the at least one direct anthraquinone dye per gram of keratin material in free form is deposited by application.

12. The method according to claim 4, wherein a quantity of at most 20 g of the at least one direct anthraquinone dye per gram of human keratin material is deposited by application.

13. The method according to claim 4, wherein a quantity of at most 10 g of the at least one direct anthraquinone dye per gram of human keratin material is deposited by application.

14. The method according to claim 4, wherein a quantity of at most 5 g of the at least one direct anthraquinone dye per gram of human keratin material is deposited by application.

15. The method according to claim 4, wherein the at least one direct anthraquinone dye is applied to the human keratin materials in the form of a divided solid, in a free form, or in a non-free form.

16. The method according to claim 4, wherein the at least one direct anthraquinone dye is applied to the human keratin materials in the form of a film.

17. The method according to claim 16, wherein the film comprises at least one film-forming polymer.

18. The method according to claim 16, wherein the film comprises at least one plasticizer.

19. The method according to claim 16, wherein the film is deposited on a support which is not degraded under the conditions for carrying out the method.

20. A dry composition, in the form of a divided or undivided solid comprising:
at least one anthraquinone dye, in a dispersed state in the dry composition, of formula (I):

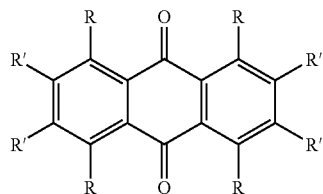

in which:

R, independently of each other, represent:

a hydrogen atom;

a hydroxyl group;

an amino group; or an amino group which is mono- or di-substituted with one or two radicals, which are identical or different, chosen from the radicals $C_1$-$C_6$ alkyl, $C_1$-$C_6$ hydroxyalkyl, and $C_6$ aryl optionally substituted with one or more $C_1$-$C_6$ alkyl radicals;

R', independently of each other, represent:

a hydrogen atom;

a halogen atom;

a hydroxyl group;

an amino group;

an amino group which is mono- or di-substituted with one or two radicals, which are identical or different, chosen from the radicals $C_1$-$C_6$ alkyl, $C_1$-$C_6$ alkylamino, $C_5$-$C_8$ cycloalkyl, and $(C_1$-$C_6)$alkoxy$(C_1$-$C_6)$alkyl;

a $C_6$ aryl radical optionally substituted with one or more groups, which are identical or different, chosen from halogen atoms and the radicals $C_1$-$C_6$ alkyl, $C_1$-$C_6$ alkoxy, and $(C_1$-$C_6)$alkoxy$(C_1$-$C_6)$alkyl;

a $(C_6)$aryloxy group;

a $(C_6)$aryloxy group substituted with a $(C_6)$aryl-$SO_3$ group, the aryl group being optionally substituted with one or more groups, which are identical or different, chosen from halogen atoms and the groups hydroxyl, trifluoromethyl, $C_1$-$C_6$ alkyl, $C_1$-$C_6$ alkoxy, $C_6$ aryl, $(C_6)$aryl$(C_1$-$C_4)$alkyl, $(C_6)$aryloxy, nitro, $C_2$-$C_6$ acyl, $(C_2$-$C_6)$acylamino, $(C_1$-$C_6)$alkylmercapto, $C_6$ thiophenyl, sulphonyloxy, and $(C_1$-$C_6)$-alkylbenzenesulphonyl;

a $(C_6)$aryloxy group substituted with a group —$SO_2N(R_a)_2$ with $R_a$, which are identical or different, representing a hydrogen atom, a radical $C_1$-$C_6$ alkyl, $C_2$-$C_6$ alkenyl, $(C_6)$aryl$(C_1$-$C_6)$alkyl, or $C_5$-$C_8$ cycloalkyl, it being possible for the two radicals $R_a$ to form, with the nitrogen atom to which they are attached, a 5-or 6-membered heterocycle;

a group —$SR_b$ with $R_b$ representing a 5-or 6-membered heterocycle, comprising the sulfur atom and optionally comprising a nitrogen, sulfur, or oxygen atom;

—$COOR_c$ with $R_c$ representing a group $C_1$-$C_4$ hydroxyalkyl, $(C_1$-$C_4)$alkylphenyl, $C_5$-$C_8$ cycloalkyl, carbonyloxy$(C_6)$aryl, or carbonyl$(C_6)$aryl;

—$SO_3$—$(C_6)$aryl, the aryl radical being optionally substituted with one or more groups, which are identical or different, chosen from halogen atoms and the groups hydroxyl, trifluoromethyl, $C_1$-$C_6$ alkyl, $C_1$-$C_6$ alkoxy, $C_6$ aryl, $(C_6)$aryl$(C_1$-$C_4)$alkyl, $(C_6)$aryloxy, nitro, $C_2$-$C_6$ acyl, $(C_2$-$C_6)$acylamino, $(C_1$-$C_6)$alkylmercapto, thiophenyl, sulphonyloxy, and $(C_1$-$C_6)$alkylbenzenesulphonyl; or at least one film-forming polymer, wherein the dry composition is in the form of a film.

21. The composition according to claim 20, wherein the at least one direct anthraquinone dye is of the following formula (Ia):

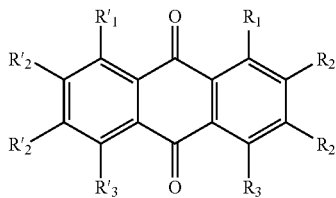

in which:

R₁ represents a hydrogen atom, a hydroxyl group, an amino group, or an amino group which is mono- or di-substituted with one or two radicals, which are identical or different, chosen from the radicals $C_1$-$C_4$ alkyl, $C_1$-$C_6$ hydroxyalkyl, and phenyl optionally substituted with one or more $C_1$-$C_4$ alkyl radicals;

R'₁ represents a hydrogen atom, a hydroxyl group, or an amino group;

R₂ and R'₂, independently of each other, represent
a hydrogen atom;
a halogen atom;
a hydroxyl group;
an amino group;
an amino group which is mono- or di-substituted with one or two radicals, which are identical or different, chosen from the radicals $C_1$-$C_6$ alkyl, $C_1$-$C_6$ alkylamino, $C_5$-$C_8$ cycloalkyl, and ($C_1$-$C_6$)alkoxy($C_1$-$C_6$)alkyl;
a $C_6$ aryl radical optionally substituted with one or more groups, which are identical or different, chosen from halogen atoms and the radicals $C_1$-$C_6$ alkyl, $C_1$-$C_6$ alkoxy, and ($C_1$-$C_6$)alkoxy($C_1$-$C_6$)alkyl; or
a ($C_6$)aryloxy group;

R₃ represents a hydrogen atom; a hydroxyl group; an amino group; or an amino group which is mono- or di-substituted with one or two radicals, which are identical or different, chosen from the radicals $C_1$-$C_6$ alkyl, $C_1$-$C_6$ hydroxyalkyl, and $C_6$ aryl optionally substituted with one or more $C_1$-$C_6$ alkyl radicals;

R'₃ represents a hydrogen atom; a hydroxyl group; or an amino group.

22. The composition according to claim 20, further comprising at least one plasticizer.

23. The composition according to claim 20, wherein the film has a thickness ranging from 0.01 mm to 2 mm.

24. The composition according to claim 23, wherein the film has a thickness ranging from 0.02 mm to 0.2 mm.

25. A method for preparing the dry composition according to claim 20, wherein a mixture comprising at least one direct anthraquinone dye, at least one film-forming polymer, and at least one solvent is applied to a support, and then the at least one solvent is evaporated.

26. The method according to claim 25, wherein the mixture comprises from 0.0001% to 60% by weight of the at least one direct anthraquinone dye.

27. The method according to claim 25, wherein the mixture comprises from 0.01% to 80% by weight of the at least one film-forming polymer.

28. The method according to claim 25, wherein the mixture comprises from 5% to 99.9% by weight of the at least one solvent.

* * * * *